(12) United States Patent
Liang (10) Patent No.: US 12,135,477 B2
(45) Date of Patent: Nov. 5, 2024

(54) GREEN LIGHT SACRIFICIAL LAYER AND METHOD OF MANUFACTURING TOUCH DISPLAY DEVICE

(71) Applicant: TCL CHINA STAR OPTOELECTRONICS TECHNOLOGY CO., LTD., Guangdong (CN)

(72) Inventor: Yuheng Liang, Guangdong (CN)

(73) Assignee: TCL CHINA STAR OPTOELECTRONICS TECHNOLOGY CO., LTD., Guangdong (CN)

( * ) Notice: Subject to any disclaimer, the term of this patent is extended or adjusted under 35 U.S.C. 154(b) by 656 days.

(21) Appl. No.: 17/593,271

(22) PCT Filed: Jun. 4, 2021

(86) PCT No.: PCT/CN2021/098362
§ 371 (c)(1),
(2) Date: Sep. 14, 2021

(87) PCT Pub. No.: WO2022/170704
PCT Pub. Date: Aug. 18, 2022

(65) Prior Publication Data
US 2023/0221596 A1    Jul. 13, 2023

(30) Foreign Application Priority Data
Feb. 10, 2021    (CN) .......................... 202110184888.9

(51) Int. Cl.
*G02F 1/1335*    (2006.01)
*C07C 245/08*    (2006.01)
(Continued)

(52) U.S. Cl.
CPC ...... *G02F 1/133516* (2013.01); *C07C 245/08* (2013.01); *C08F 120/36* (2013.01);
(Continued)

(58) Field of Classification Search
CPC ........... G06F 2203/04103; G06F 3/041; G06F 3/0412; C08F 120/36; C07C 245/08; G02F 1/13338; G02F 1/133516
See application file for complete search history.

(56) References Cited

U.S. PATENT DOCUMENTS

2015/0155297 A1    6/2015    Eom et al.
2017/0256594 A1    9/2017    Bae et al.

FOREIGN PATENT DOCUMENTS

CN    106066731 A    11/2016
CN    107132942 A    9/2017
(Continued)

OTHER PUBLICATIONS

Translation of KR20130130483 (Year: 2013).*
(Continued)

*Primary Examiner* — Sonya M Sengupta (57) ABSTRACT

A green light sacrificial layer and a method for manufacturing a touch display panel are disclosed. The green light sacrificial layer is made of a green light sacrificial layer material. A material of the green light sacrificial layer comprises an azobenzene derivative. The green light sacrificial layer is applied to the preparation of the touch display panel, thereby preventing the touch display panel from being damaged during a manufacturing process and enhancing the performance of the touch display panel.

20 Claims, 6 Drawing Sheets

(51) Int. Cl.
 *C08F 120/36* (2006.01)
 *G02F 1/1333* (2006.01)
 *G06F 3/041* (2006.01)

(52) U.S. Cl.
 CPC .......... *G02F 1/13338* (2013.01); *G06F 3/041* (2013.01); *G06F 2203/04103* (2013.01)

(56) References Cited

FOREIGN PATENT DOCUMENTS

| | | |
|---|---|---|
| CN | 107491226 A | 12/2017 |
| CN | 108281549 A | 7/2018 |
| CN | 108774151 A | 11/2018 |
| CN | 110426877 A | 11/2019 |
| CN | 111129350 A | 5/2020 |
| CN | 111333023 A | 6/2020 |
| CN | 112010775 A | 12/2020 |
| CN | 112270895 A | 1/2021 |

OTHER PUBLICATIONS

International Search Report in International application No. PCT/CN2021/098362, mailed on Nov. 9, 2021.
Written Opinion of the International Search Authority in International application No. PCT/CN2021/098362, mailed on Nov. 9, 2021.
Chinese Office Action issued in corresponding Chinese Patent Application No. 202110184888.9 dated Nov. 18, 2022, pp. 1-9.

* cited by examiner

GREEN LIGHT SACRIFICIAL LAYER AND METHOD OF MANUFACTURING TOUCH DISPLAY DEVICE

FIELD OF INVENTION

The present disclosure relates to the technical field of display, and particularly, to a green light sacrificial layer and a method of manufacturing a touch display device.

BACKGROUND OF INVENTION

With the development of technology, display devices are gradually becoming multifunctional. Touch display devices are one direction of the development. The touch display panel is usually made of a combination of a display panel and a touch module.

At present, in order to reduce a thickness of the overall films of the touch display panel, the touch module is usually manufactured on an external side of the display panel, thereby reducing a transparent substrate and an adhesive layer of the touch module. However, if the touch display panel is manufactured by such a method, and the touch module is manufactured after the display panel is completed, the touch module will undergo a chemical vapor deposition process/physical vapor deposition process/printing and dyeing process, and be exposed to high temperature/vacuum/chemical agent processes, the performance of a frame glue of the display panel will be affected, and the frame glue will easily peel off and dissolve, which may cause a problem of separation between an upper glass and a lower glass of the display panel. If the display panel is assembled and then undergoes a process of manufacturing the touch module, an equipment, such as a vacuum suction washing, curling, etc., in the process of manufacturing the touch module may create local pressures on the display panel, and these pressures will cause problems of damaging a support structure of the display panel or crushing circuits of the support structure, thereby affecting the performance of the touch display panel.

Even if the touch module is manufactured by a dual-sided process of a color filter substrate, followed by assembling the touch module and the display panel to prepare the touch display panel, in a step of removing a scratch-resistant protective layer, the scratch-resistant protective layer is usually removed with a high temperature and high concentration lye since photoresists, such as acrylate and polysiloxane, are usually used as the scratch-resistant protective layer. However, the high temperature and high concentration lye are prone to damage the touch module, thereby causing the failure of a touch function.

Technical Problems

The embodiments of the present disclosure provide a green light sacrificial layer and a method for manufacturing a touch display panel, which may enhance the performance of the touch display panel.

SUMMARY OF INVENTION

Technical Solutions

One embodiment of the present disclosure provides a green light sacrificial layer. The green light sacrificial layer is made of a green light sacrificial layer material. The green light sacrificial layer material comprises an azobenzene derivative, and a structural formula of the azobenzene derivative is one or a combination of and wherein $n=20$-$50$, the $R_1$ group is selected from one of $-C_mH_{2m}-$, $m=5$-$17$, the $R_2$ group is selected from one of $-C_yH_{2y+1}$, $y=5$-$18$, the $R_3$ group, the $R_4$ group, and the $R_5$ group are selected from one or a combination of $-C_xH_{2x+1}$, $x=1$-$20$.

Optionally, in some embodiments of the present disclosure, the $R_1$ group is $-C_6H_{12}-$, the $R_2$ group is $-C_{10}H_{21}$, the $R_3$ group, the $R_4$ group, and the $R_5$ group are $-C_5H_{11}$.

Optionally, in some embodiments of the present disclosure, in a situation that the green light sacrificial layer is made of a mixture of two materials, a mass ratio of is $1$-$5$:$1$-$6.5$.

Optionally, in some embodiments of the present disclosure, the green light sacrificial layer is applied to an external side of a dual-sided process of a color filter substrate.

Optionally, in some embodiments of the present disclosure, a thickness of the green light sacrificial layer ranges from 1 nm to 10,000 nm.

A method for manufacturing a touch display panel comprises steps of:
  providing a color filter substrate, wherein one side of the color filter substrate is sequentially provided with a touch module and a green light sacrificial layer;
  providing a light emitting substrate, wherein a light emitting side of the light emitting substrate is attached to the side of the color filter substrate away from the green light sacrificial layer;
  irradiating the green light sacrificial layer with a green light; and
  removing the green light sacrificial layer from the touch module to obtain a touch display panel.

Optionally, in some embodiments of the present disclosure, the green light sacrificial layer is made of an azobenzene derivative. A structural formula of the azobenzene derivative is one or a combination of and wherein n=20-50, the $R_1$ group is selected from one of —$C_mH_{2m}$—, m=5-17, the $R_2$ group is selected from one of —$C_yH_{2y+1}$, y=5-18, the $R_3$ group, the $R_4$ group, and the $R_5$ group are selected from one or a combination of —$C_xH_{2x+1}$, x=1-20.

Optionally, in some embodiments of the present disclosure, a wavelength of the green light ranges from 480 nm to 600 nm.

Optionally, in some embodiments of the present disclosure, a thickness of the green light sacrificial layer ranges from 0.1 μm to 10, μm.

Optionally, in some embodiments of the present disclosure, a step of "providing a color filter substrate, wherein one side of the color filter substrate is sequentially provided with a touch module and a green light sacrificial layer" comprises a step of:
  forming a protective layer on the side of the green light sacrificial layer away from the touch module.

Optionally, in some embodiments of the present disclosure, steps of "irradiating the green light sacrificial layer with a green light and removing the green light sacrificial layer from the touch module to obtain a touch display panel" comprise steps of:
  irradiating the green light sacrificial layer with the green light; and
  removing the green light sacrificial layer and the protective layer from the touch module.

Optionally, in some embodiments of the present disclosure, a removing agent used for removing the green light sacrificial layer comprises one or a combination of ethanol, water, toluene, and acetone.

Optionally, in some embodiments of the present disclosure, a duration for irradiating the green light sacrificial layer with the green light ranges from 5 minutes to 60 minutes.

Optionally, in some embodiments of the present disclosure, a step of "providing a color filter substrate, wherein one side of the color filter substrate is sequentially provided with a touch module and a green light sacrificial layer" comprises steps of:
  sequentially stacking a first touch wiring layer, a first insulating layer, a second touch wiring layer, a second insulating layer, and the green light sacrificial layer on one side of the color filter substrate, wherein the first touch wiring layer, the first insulating layer, the second touch wiring layer, and the second insulating layer constitute the touch module.

Optionally, in some embodiments of the present disclosure, a material of the first touch wiring layer comprises one or a combination of Mo, Cu, Al, Ti, and Ag.

Optionally, in some embodiments of the present disclosure, a material of the second touch wiring layer comprises one or a combination of Mo, Cu, Al, Ti, and Ag.

Optionally, in some embodiments of the present disclosure, a material of the first insulating layer comprises one or a combination of SixOy, SixNy, and SiOxNy.

Optionally, in some embodiments of the present disclosure, a material of the second insulating layer comprises one or a combination of SixOy, SixNy, and SiOxNy.

Optionally, in some embodiments of the present disclosure, the step of "providing a color filter substrate, wherein one side of the color filter substrate is sequentially provided with a touch module and a green light sacrificial layer" comprises a step of:
  disposing a light shielding layer on another side of the color filter substrate.

Optionally, in some embodiments of the present disclosure, after a step of "disposing a light shielding layer on another side of the color filter substrate", the method further comprises a step of:
  disposing a conductive layer on one side of the light shielding layer away from the touch module.

Beneficial Effects

The embodiment of the present disclosure discloses a green light sacrificial layer and a method for manufacturing a touch display panel. The green light sacrificial layer is made of a green light sacrificial layer material. The green light sacrificial layer material comprises an azobenzene derivative. The green light sacrificial layer is applied to the preparation of the touch display panel, thereby preventing the touch display panel from being damaged during a manufacturing process and enhancing the performance of the touch display panel.

BRIEF DESCRIPTION OF DRAWINGS

In order to explain the technical solutions of the present disclosure more clearly, the following will briefly introduce the drawings needed in the description of the embodiments. Obviously, the drawings in the following description are merely some embodiments of the present disclosure. For those skilled in the art, without creative work, other drawings can be obtained based on these drawings.

DETAILED DESCRIPTION OF PREFERRED EMBODIMENTS

The following will clearly and completely describe the technical solutions in the embodiments of the present disclosure with reference to the drawings in the embodiments of the present disclosure. Obviously, the described embodiments are only one portion of the embodiments of the present disclosure, rather than all of the embodiments. Based on the embodiments in the present disclosure, all other embodiments obtained by those skilled in the art without creative work are within claimed scope of the present disclosure. In addition, it should be understood that the specific embodiments described herein are merely used to irradiate and explain the present disclosure and are not used to limit the present disclosure. In the present disclosure, if no explanation is made to the contrary, orientation terms used such as "upper" and "lower" generally refer to upper and lower positions of the device in actual use or working condition, and specifically refer to directions of figures in the drawings. Moreover, terms of "inner" and "outer" refer to an outline of the device.

One embodiment of the present disclosure provides a green light sacrificial layer 10 and a touch display panel 20, which will be described in detail below. It should be noted that an order of description in the following embodiments does not tend to limit a preferred order of the embodiments.

Figure 1:
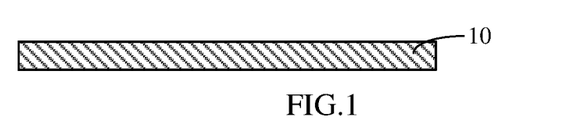
FIG. 1 is a schematic cross-sectional view of a green light sacrificial layer provided by one embodiment of the present disclosure.

Please refer to FIG. 1. FIG. 1 is a schematic cross-sectional view of a green light sacrificial layer provided by one embodiment of the present disclosure. One embodiment of the present disclosure provides the green light sacrificial layer 10, which is described specifically as follows.

The green light sacrificial layer 10 is made of the green light sacrificial layer 10 material. The green light sacrificial layer 10 material comprises an azobenzene derivative, and a structural formula of the azobenzene derivative is one or a combination of and and wherein n=20-50, the $R_1$ group is selected from one of $-C_mH_{2m}-$, m=5-17, the $R_2$ group is selected from one of $-C_yH_{2y+1}$, y=5-18, the $R_3$ group, the $R_4$ group, and the $R_5$ group are selected from $-C_xH_{2x+1}$, x=1-20. In some embodiments, at least two of the $R_3$ group, $R_4$ group, and $R_5$ group may be the same. In other embodiments, the $R_3$ group, $R_4$ group, and $R_5$ group may be different.

In one embodiment, the $R_1$ group is $-C_6H_{12}-$, the $R_2$ group is $-C_{10}H_{21}$, the $R_3$ group, the $R_4$ group, and the $R_5$ group are $-C_5H_{11}$.

In one embodiment, the $R_1$ group is $-C_6H_{12}-$ and the $R_2$ group is $-C_{10}H_{21}$. The structural formula of the azobenzene derivative is In one embodiment, when the green light sacrificial layer 10 is irradiated with a green light, a state of the green light sacrificial layer 10 converts from a solid state to a liquid state. That is, converting from a structural formula of trans-azobenzene derivative to a structural formula of cis-azobenzene derivative to remove the green light sacrificial layer 10.

In one embodiment, the $R_1$ group is —$C_6H_{12}$— and the $R_2$ group is —$C_{16}H_{33}$. The structural formula of the azobenzene derivative is In one embodiment, when the green light sacrificial layer 10 is irradiated with the green light, the state of the green light sacrificial layer 10 converts from the solid state to the liquid state. That is, converting from the structural formula of trans-azobenzene derivative to the structural formula of cis-azobenzene derivative to remove the green light sacrificial layer 10.

In one embodiment, the $R_3$ group, the $R_4$ group, and the $R_5$ group are —$C_5H_{11}$. The structural formula of the azobenzene derivative is In one embodiment, when the green light sacrificial layer 10 is irradiated with the green light, the state of the green light sacrificial layer 10 converts from the solid state to the liquid state. That is, converting from the structural formula of trans-azobenzene derivative to the structural formula of cis-azobenzene derivative to remove the green light sacrificial layer 10.

In one embodiment, the $R_3$ group, the $R_4$ group, and the $R_5$ group are —$C_{12}H_{25}$. The structural formula of the azobenzene derivative is

In one embodiment, when the green light sacrificial layer 10 is irradiated with the green light, the state of the green light sacrificial layer 10 converts from the solid state to the liquid state. That is, converting from the structural formula of trans-azobenzene derivative to the structural formula of cis-azobenzene derivative to remove the green light sacrificial layer 10.

In one embodiment, the $R_3$ group is —$C_7H_{15}$, the $R_4$ group is —$C_{10}H_{21}$, and the $R_5$ group is —$C_{16}H_{33}$. The structural formula of the azobenzene derivative is In one embodiment, when the green light sacrificial layer 10 is irradiated with the green light, the state of the green light sacrificial layer 10 converts from the solid state to the liquid state. That is, converting from the structural formula of trans-azobenzene derivative to the structural formula of cis-azobenzene derivative to remove the green light sacrificial layer 10.

In one embodiment, in a situation that the green light sacrificial layer is made of a mixture of and a mass ratio of is 1-5:1-6.5. Specifically, the mass ratio of may be 1:1, 1:2, 1.4:3, 3:4.3 or 4.5:6, etc.

In one embodiment, the green light sacrificial layer 10 may be applied to an external side of a dual-sided process of a color filter substrate.

In one embodiment, a thickness of the green light sacrificial layer ranges from 1 nm to 10,000 nm.

The present disclosure provides a green light sacrificial layer. The green light sacrificial layer 10 is made of an azobenzene derivative. The green light sacrificial layer 10 is applied to an electronic device, and the green light sacrificial layer 10 merely needs to be irradiated with a green light. The green light sacrificial layer 10 may undergo state conversion under irradiation of the green light. That is, under irradiation of the green light, the green light sacrificial layer 10 converts from a solid state to a liquid state, so that the green light sacrificial layer 10 may be removed without treating with a high temperature and high concentration lye, thereby ensuring the performance of an electric device and reducing the cost.

Figure 2:
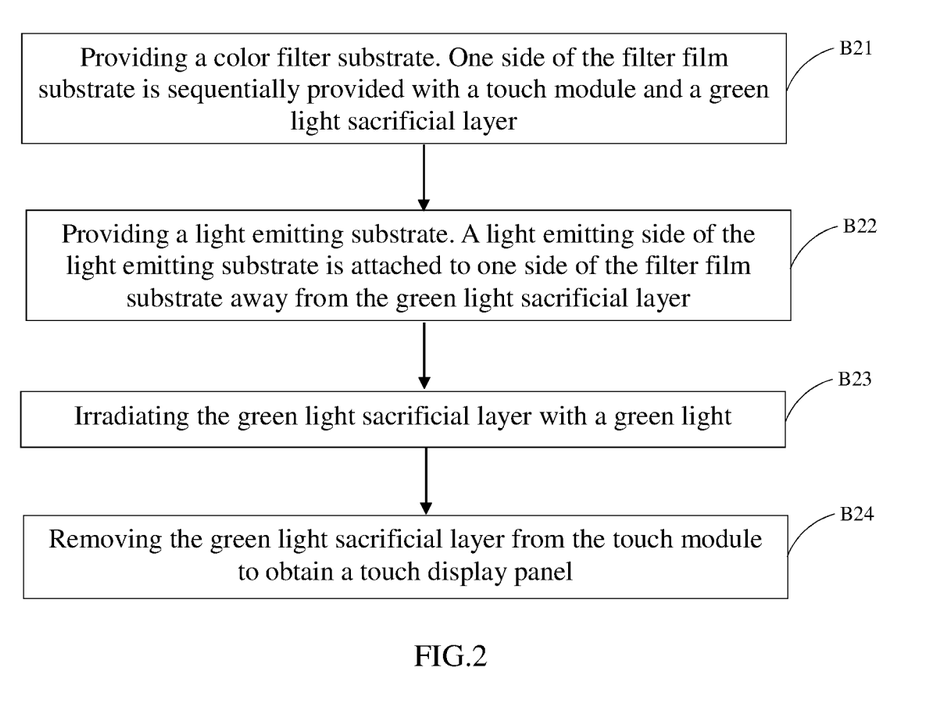
FIG. 2 is a flow chart of a method for manufacturing a touch display panel provided by one embodiment of the present disclosure.

Please refer to FIG. 2 and FIG. 3 to FIG. 8. FIG. 2 is a flow chart of a method for manufacturing a touch display panel provided by one embodiment of the present disclosure. FIG. 3 to FIG. 8 are first schematic cross-sectional views of first process of the method for manufacturing the touch display panel provided by one embodiment of the present disclosure. The present disclosure further provides a method for manufacturing a touch display panel 20, which is described specifically as follows.

Step B21: providing a color filter substrate. One side of the color filter substrate is sequentially provided with a touch module and a green light sacrificial layer.

Figure 3:
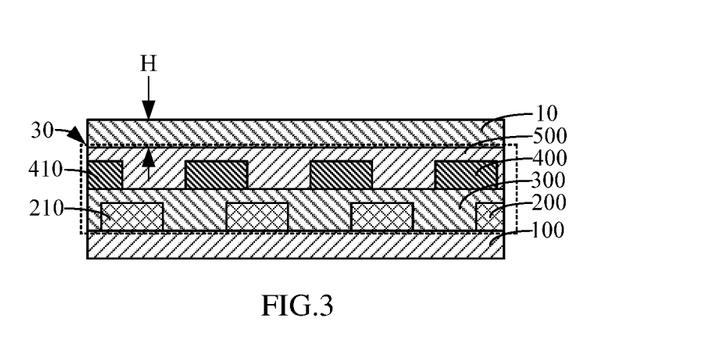
FIG. 3 to FIG. 8 are first schematic cross-sectional views of first process of the method for manufacturing the touch display panel provided by one embodiment of the present disclosure.

Please refer to FIG. 3. Specifically, a color filter substrate is provided. A first touch wiring layer 200, a first insulating layer 300, a second touch wiring layer 400, and a second insulating layer 500 are sequentially stacked on one side of the color filter substrate 100. A material of the color filter substrate 100 comprises polyimide, but is not limited thereto. The first touch wiring layer 200 comprises a plurality of first touch wiring portions 210. A material of the first touch wiring layer 200 comprises one or a combination of Mo, Cu, Al, Ti, and Ag. The second touch wiring layer 400 comprises a plurality of second touch wiring portions 410. A material of the second touch wiring layer 400 comprises one or a combination of Mo, Cu, Al, Ti, and Ag. A material of the first insulating layer 300 comprises one or a combination of SixOy, SixNy, and SiOxNy. A material of the second insulating layer 500 comprises one or a combination of SixOy, SixNy, and SiOxNy.

The first touch wiring layer 200, the first insulating layer 300, the second touch wiring layer 400, and the second insulating layer 500 constitute the touch module 30.

Then, the green light sacrificial layer 10 is disposed on the second insulating layer 500. The green light sacrificial layer 10 is made of the green light sacrificial layer 10 material.

In one embodiment, the green light sacrificial layer 10 material comprises an azobenzene derivative. A structure of the azobenzene derivative is one or a combination of and wherein n=20-50, the $R_1$ group is selected from one of $-C_mH_{2m}-$, m=5-17, the $R_2$ group is selected from $-C_yH_{2y+1}$, y=5-18, the $R_3$ group, the $R_4$ group, and the $R_5$ group are selected from $-C_xH_{2x+1}$, x=1-20. In some embodiments, at least two of the $R_3$ group, $R_4$ group, and $R_5$ group may be the same. In other embodiments, the $R_3$ group, $R_4$ group, and $R_5$ group may be different.

In one embodiment, the green light sacrificial layer 10 is a protective layer for protecting a structure in the touch display panel 20, so that the subsequent manufacturing process may proceed stably.

In one embodiment, a thickness H of the green light sacrificial layer 10 ranges from 0.1 μm to 10, μm.

In one embodiment, the thickness H of the green light sacrificial layer 10 may be 0.2 μm, 0.6 μm, 1 μm, 5 μm, 8 μm or 9 μm.

Figure 4:
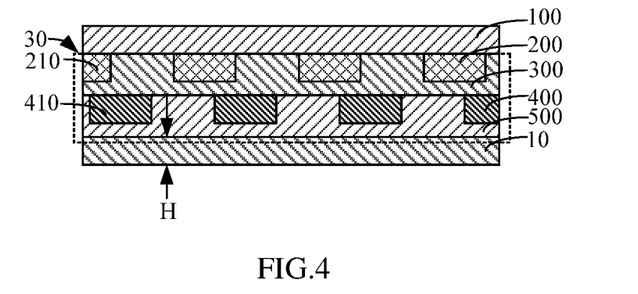

Please refer to FIG. 4. The color filter substrate 100, the touch module 30, and the green light sacrificial layer 10 are turned over.

Figure 5:
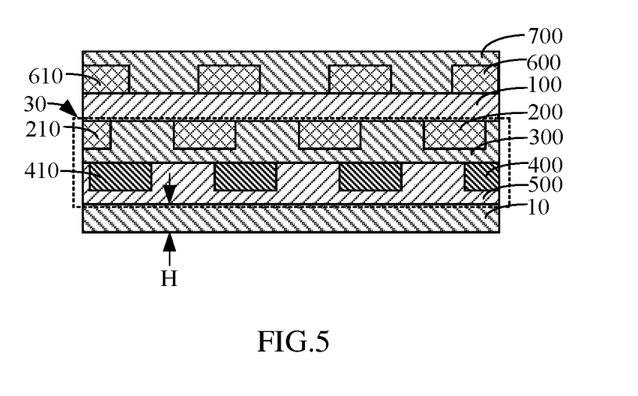

Please refer to FIG. 5. A light shielding layer 600 and a conductive layer 700 are sequentially stacked on another side of the color filter substrate 100. The light shielding layer 600 comprises a light shielding portion 610. The conductive layer 700 is made of indium tin oxide (ITO).

Figure 6:
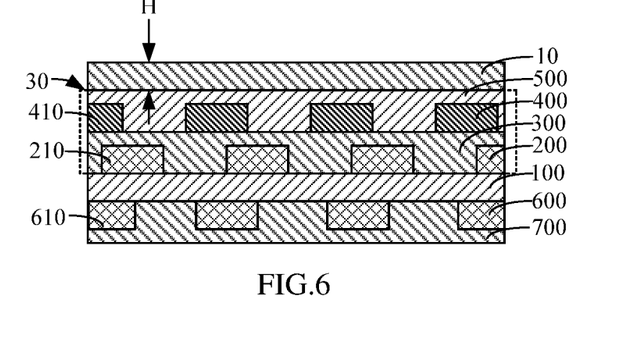

Please refer to FIG. 6. The color filter substrate 100, the touch module 30, the green light sacrificial layer 10, the light shielding layer 600, and the conductive layer 700 are turned over.

Step B22: providing a light emitting substrate. A light emitting side of the light emitting substrate is attached to one side of the color filter substrate away from the green light sacrificial layer.

Figure 7:
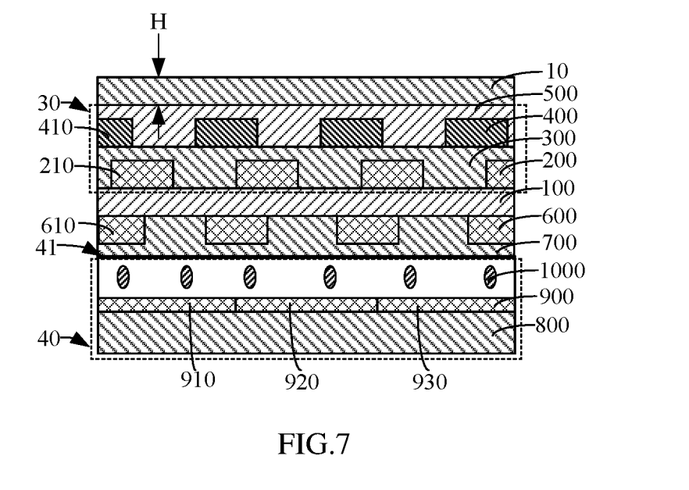

Please refer to FIG. 7. A light emitting substrate 40 is provided. The light emitting substrate 40 comprises an array device layer 800, a color resist layer 900, and a liquid crystal layer 1000. The color resist layer 900 and the liquid crystal layer 1000 are sequentially stacked on the array device layer 800. The color resist layer 900 comprises a first color resist layer 910, a second color resist layer 920, and a third color resist layer 930. The second color resist layer 920 is disposed between the first color resist layer 910 and the third color resist layer 930. The first color resist layer 910 comprises one of a red color resist layer, a green color resist layer, and a blue color resist layer. The second color resist layer 920 comprises one of the red color resist layer, the green color resist layer, and the blue color resist layer. The third color resist layer 930 comprises one of the red color resist layer, the green color resist layer, and the blue color resist layer. The first color resist layer 910, the second color resist layer 920, and the third color resist layer 930 have different color resist layers. A light emitting side 41 of the light emitting substrate 40 is attached to the conductive layer 700 of the color filter substrate 100. That is, the liquid crystal layer 1000 of the light emitting substrate 40 is attached to the conductive layer 700 of the color filter substrate 100.

Step B23: irradiating the green light sacrificial layer with the green light.

Step B24: removing the green light sacrificial layer from the touch module to obtain the touch display panel.

Figure 8:
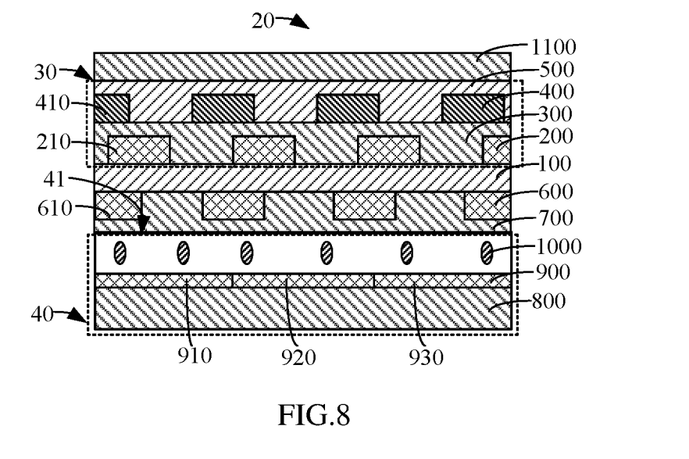
Figure 9:
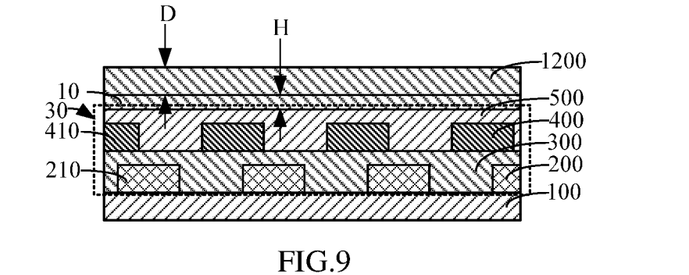
FIG. 9 to FIG. 14 are second schematic cross-sectional views of second process of the method for manufacturing the touch display panel provided by one embodiment of the present disclosure.
Figure 10:
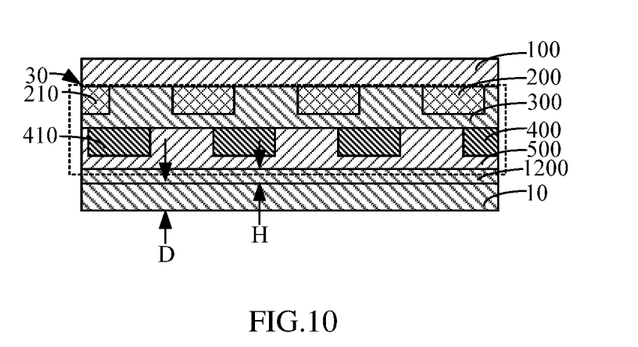
Figure 11:
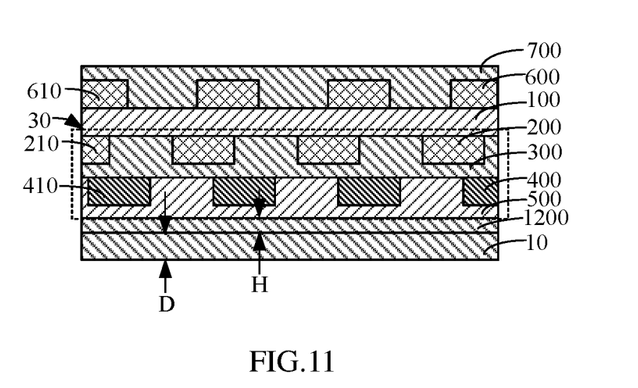
Figure 12:
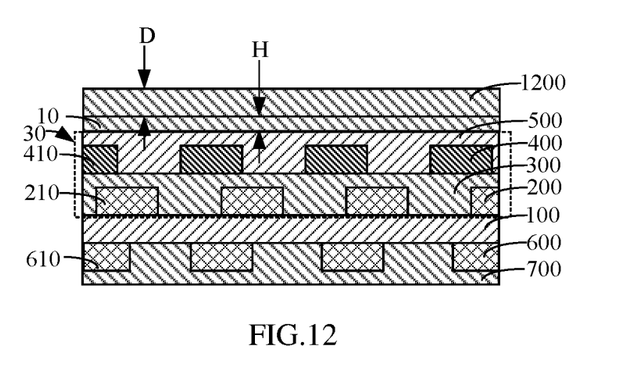
Figure 13:
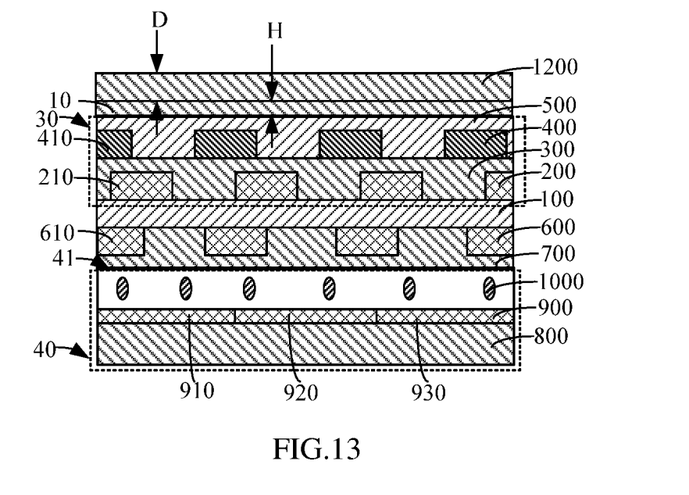
Figure 14:
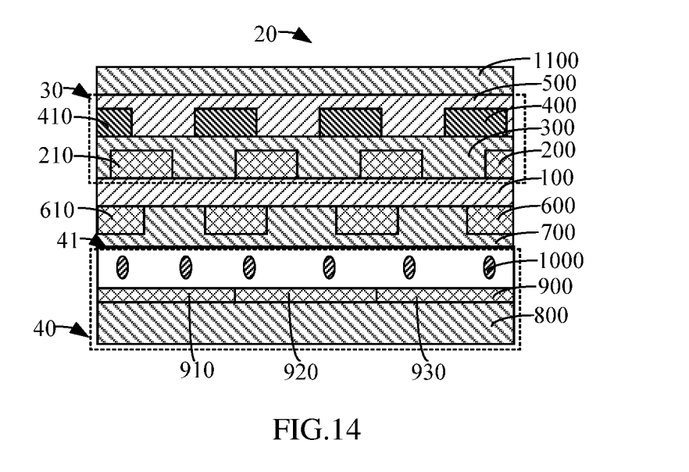

Please refer to FIG. 8. Specifically, the green light sacrificial layer 10 is irradiated with the green light having a wavelength of from 480 nm to 600 nm. The green light sacrificial layer 10 may convert from a solid state to a liquid state under the irradiation of the green light. The liquid green light sacrificial layer 10 is then removed with a removing agent, and the green light sacrificial layer 10 is removed from the second insulating layer 500 to form the touch display panel 20.

In one embodiment, a duration for irradiating the green light sacrificial layer with the green light ranges from 5 minutes to 60 minutes. Specifically, the duration for irradiating the green light sacrificial layer with the green light may be 6 minutes, 10 minutes, 20 minutes, 35 minutes, 47 minutes or 53 minutes, etc.

In one embodiment, the green light sacrificial layer 10 is irradiated with green light. The green light sacrificial layer 10 is converted from the solid state to the liquid state. The green light sacrificial layer is then removed from the second insulating layer 500 with the removing agent. The removing agent comprises one or a combination of ethanol, water, toluene, and acetone.

In one embodiment, the green light sacrificial layer 10 is irradiated with green light having a wavelength of from 500 nm to 550 nm, and the green light sacrificial layer 10 is removed from the second insulating layer 500.

In one embodiment, after step B24, the method further comprises a step of:
  disposing a packaging cover plate 1100 on the second insulating layer 500.

In the present disclosure, by irradiating the green light sacrificial layer with the green light, the green light sacrificial layer is converted from a solid state to a liquid state under the irradiation of green light. The green light sacrificial layer may be then removed from the second insulating layer with a common removing agent. That is, ethanol, water, toluene, and acetone. It does not need to use a high temperature and high concentration lye to remove the green light sacrificial layer from the second insulating layer, thereby avoiding a conventional touch display panel to be damage as the touch module is formed by a dual-sided process of a color filter substrate, and then is assembled with the display panel, followed by using the high temperature and high concentration lye to remove a protective layer. As a result, the touch function of the touch module is failure, and the performance of the touch display panel is enhanced.

Please refer to FIG. 9 to FIG. 14. FIGS. 9-14 are second schematic cross-sectional views of second process of the method for manufacturing the touch display panel provided by one embodiment of the present disclosure. It should be noted that the difference between second cross-sectional schematic view of second process and first cross-sectional schematic view of first process is that:
  In step B21, the method comprises a step of:
    forming a protective layer 1200 on the side of the green light sacrificial layer 10 away from the touch module 30. The green light sacrificial layer 10 adheres the protective layer 1200 to the second insulating layer 500. The protective layer 1200 is used to protect a structure in the touch module 30, so that the subsequent manufacturing process may proceed stably.
  The green light sacrificial layer 10 is then irradiated with green light, and the green light sacrificial layer 10 and the protective layer 1200 are removed from the touch module 30.

In one embodiment, a thickness H of the green light sacrificial layer ranges from 1 nm to 1000 nm.

In one embodiment, the thickness H of the green light sacrificial layer may be 20 nm, 80 nm, 200 nm, 500 nm, 800 nm, 900 nm, 980 nm, etc.

In one embodiment, a thickness D of the protective layer 1200 ranges from 1 μm to 50 μm.

In one embodiment, the thickness D of the protective layer 1200 may be 1.1 m, 1.3 m, 8 m, 20 m, 35 m, 46 m, 49.1 m, etc.

Figure 15:
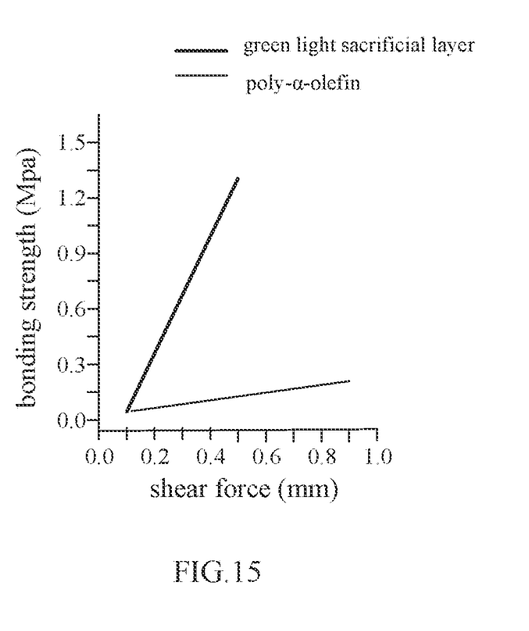
FIG. 15 is a stress-strain curve of the green light sacrificial layer provided by one embodiment of the present disclosure.

Please refer to FIG. 15. FIG. 15 is a stress-strain curve of the green light sacrificial layer provided by one embodiment of the present disclosure. A space between two glass plates is filled with a melted 5 mg green light sacrificial layer 10, and the two glass plates are connected to an uniform layer of the green light sacrificial layer 10, with an overlapping area of 2.5 cm×0.7 cm, and then cooled at room temperature. A shear force is then applied to the plates. After repeated tests, such as 30 tests, the two glass plates still cannot be pulled apart before they break. The glass plate is then replaced with a hard aluminum alloy plate, followed by proceeding a further test. A maximum bonding strength of the green light sacrificial layer 10 is measured as 1.34 MPa. In contrast, an amorphous poly-α-olefin arranged between the hard aluminum alloy plates, and a bonding strength of the amorphous poly-α-olefin is measured as 0.17 MPa, which is one-eighth of the green light sacrificial layer 10. It is clear that the green light sacrificial layer 10 has strong adhesion.

In addition, the green light sacrificial layer 10 bears a weight of 11.15 kg in 2 minutes, which indicates that the green light sacrificial layer 10 has high stability when used as an adhesive layer.

In the present disclosure, the green light sacrificial layer 10 is used to adhere the protective layer 1200 to the second insulating layer 500 to protect the touch module 30 and the light emitting substrate 40 in the touch display panel 20. Moreover, the green light sacrificial layer 10 may be converted from a solid state to a liquid state by irradiating the green light sacrificial layer with the green light, so that the green light sacrificial layer 10 and the protective layer 1200 are removed from the second insulating layer 500 without treatment with the high temperature and high concentration lye. The touch module 30 is prevented from being affected by high temperature and high concentration lye, thereby improving the performance of the touch display panel 20, thinning the touch display panel 20, and reducing the cost.

The embodiment of the present disclosure discloses a green light sacrificial layer and a method for manufacturing a touch display panel. The green light sacrificial layer is made of a green light sacrificial layer material. The green light sacrificial layer material comprises an azobenzene derivative. The green light sacrificial layer may be converted from a solid state to a liquid state under the irradiation of a green light. The green light sacrificial layer is a protective layer. By applying the green light sacrificial layer to a manufacturing process of the touch display panel, the green light sacrificial layer in the solid state may protect a structure of the touch display panel, so that the subsequent manufacturing process may proceed stably. The green light is used to irradiate the green light sacrificial layer, and the green light sacrificial layer may be converted from the solid state to the liquid state, so that the green light sacrificial layer may be removed from the second insulating layer, thereby avoiding the touch display panel to be damaged and enhancing the performance of the touch display panel. The green light sacrificial layer is an adhesive layer. By applying the green light sacrificial layer to the manufacturing process of the touch display panel, the green light sacrificial layer is used to adhere the protective layer to the second insulating layer. The protective layer may protect a structure in the touch display panel. The green light is used to irradiate the green light sacrificial layer, and the green light sacrificial layer may be converted from the solid state to the liquid state, so that the green light sacrificial layer and the protective layer may be removed from the second insulating layer, thereby avoiding the touch display panel to be damaged and enhancing the performance of the touch display panel.

A green light sacrificial layer and a method for manufacturing a touch display panel are described in detail above. Specific examples are used herein to describe the principles and implementations of the present disclosure, and the description of the embodiment above is merely used to help understand the method of the present disclosure and the core concept thereof. Moreover, for those skilled in the art, according to the concept of the present disclosure, there will be changes in the specific embodiments and the scope of application. In summary, the content of the specification should not be construed as a limitation to the present disclosure.

What is claimed is:

1. A green light sacrificial layer, wherein the green light sacrificial layer is made of a green light sacrificial layer material, the green light sacrificial layer material comprises an azobenzene derivative, and a structural formula of the azobenzene derivative is one or a combination of and wherein n=20-50, the $R_1$ group is selected from one of —$C_mH_{2m}$—, m=5-17, the $R_2$ group is selected from one of —$C_yH_{2y+1}$, y=5-18, the $R_3$ group, the $R_4$ group and the $R_5$ group are selected from one or a combination of —$C_xH_{2x+1}$, x=1-20.

2. The green light sacrificial layer according to claim 1, wherein the $R_1$ group is —$C_6H_{12}$—, the $R_2$ group is —$C_{10}H_{21}$, the $R_3$ group, the $R_4$ group and the $R_5$ group are —$C_5H_{11}$.

3. The green light sacrificial layer according to claim 1, wherein in a situation that the green light sacrificial layer is made of a mixture of two materials, a mass ratio of is 1-5:1-6.5.

4. The green light sacrificial layer according to claim 1, wherein the green light sacrificial layer is applied to an external side of a dual-sided process of a color filter substrate.

5. The green light sacrificial layer according to claim 1, wherein a thickness of the green light sacrificial layer ranges from 1 nm to 10,000 nm.

6. A method for manufacturing a touch display panel, comprising steps of:
providing a color filter substrate, wherein one side of the color filter substrate is sequentially provided with a touch module and a green light sacrificial layer;
providing a light emitting substrate, wherein a light emitting side of the light emitting substrate is attached to the side of the color filter substrate away from the green light sacrificial layer;
irradiating the green light sacrificial layer with a green light; and
removing the green light sacrificial layer from the touch module to obtain a touch display panel.

7. The method for manufacturing the touch display panel according to claim 6, wherein the green light sacrificial layer is made of an azobenzene derivative, and a structural formula of the azobenzene derivative is one or a combination of and wherein n=20-50, the $R_1$ group is selected from one of $-C_mH_{2m}-$, m=5-17, the $R_2$ group is selected from one of $-C_yH_{2y+1}$, y=5-18, the $R_3$ group, the $R_4$ group and the $R_5$ group are selected from one or a combination of $-C_xH_{2x+1}$, x=1-20.

8. The method for manufacturing the touch display panel according to claim 6, wherein a wavelength of the green light ranges from 480 nm to 600 nm.

9. The method for manufacturing the touch display panel according to claim 6, wherein a thickness of the green light sacrificial layer ranges from 0.1 μm to 10, μm.

10. The method for manufacturing the touch display panel according to claim 6, wherein a step of "providing a color filter substrate, wherein one side of the color filter substrate is sequentially provided with a touch module and a green light sacrificial layer" comprises a step of:
forming a protective layer on the side of the green light sacrificial layer away from the touch module.

11. The method for manufacturing the touch display panel according to claim 10, wherein steps of "irradiating the green light sacrificial layer with a green light and removing the green light sacrificial layer from the touch module to obtain a touch display panel" comprise steps of:
irradiating the green light sacrificial layer with the green light; and
removing the green light sacrificial layer and the protective layer from the touch module.

12. The method for manufacturing the touch display panel according to claim 6, wherein a removing agent used for removing the green light sacrificial layer comprises one or a combination of ethanol, water, toluene, and acetone.

13. The method for manufacturing the touch display panel according to claim 6, wherein a duration for irradiating the green light sacrificial layer with the green light ranges from 5 minutes to 60 minutes.

14. The method for manufacturing the touch display panel according to claim 6, wherein a step of "providing a color filter substrate, wherein one side of the color filter substrate is sequentially provided with a touch module and a green light sacrificial layer" comprises steps of:
sequentially stacking a first touch wiring layer, a first insulating layer, a second touch wiring layer, a second insulating layer, and the green light sacrificial layer on one side of the color filter substrate, wherein the first touch wiring layer, the first insulating layer, the second touch wiring layer, and the second insulating layer constitute the touch module.

15. The method for manufacturing the touch display panel according to claim 14, wherein a material of the first touch wiring layer comprises one or a combination of Mo, Cu, Al, Ti, and Ag.

16. The method for manufacturing the touch display panel according to claim 14, wherein a material of the second touch wiring layer comprises one or a combination of Mo, Cu, Al, Ti, and Ag.

17. The method for manufacturing the touch display panel according to claim 14, wherein a material of the first insulating layer comprises one or a combination of SixOy, SixNy, and SiOxNy.

18. The method for manufacturing the touch display panel according to claim 14, wherein a material of the second insulating layer comprises one or a combination of SixOy, SixNy, and SiOxNy.

19. The method for manufacturing the touch display panel according to claim 6, wherein the step of "providing a color filter substrate, wherein one side of the color filter substrate is sequentially provided with a touch module and a green light sacrificial layer" comprises a step of:
- disposing a light shielding layer on another side of the color filter substrate.

20. The method for manufacturing the touch display panel according to claim 19, wherein after a step of "disposing a light shielding layer on another end of the color filter substrate", the method further comprises a step of:
- disposing a conductive layer on one side of the light shielding layer away from the touch module.

* * * * *